United States Patent [19]

Mrozik et al.

[11] 4,206,205

[45] Jun. 3, 1980

[54] MONOSACCHARIDE AND AGLYCONE DERIVATIVES OF C-076

[75] Inventors: Helmut H. Mrozik, Matawan; George Albers-Schonberg, Princeton, both of N.J.

[73] Assignee: Merck & Co., Inc., Rahway, N.J.

[21] Appl. No.: 896,867

[22] Filed: Apr. 17, 1978

Related U.S. Application Data

[63] Continuation-in-part of Ser. No. 838,602, Oct. 3, 1977, abandoned.

[51] Int. Cl.$^2$ .................. A61K 31/71; A61K 31/365; C07H 17/08
[52] U.S. Cl. ................ 424/180; 260/343.41; 424/279; 424/181; 536/4; 536/9; 536/17 A
[58] Field of Search ................. 536/9, 17, 4; 424/180, 424/279; 260/343.41

[56] References Cited

U.S. PATENT DOCUMENTS

| | | | |
|---|---|---|---|
| 3,923,784 | 12/1975 | Kierstead et al. | 536/9 |
| 3,928,387 | 12/1975 | Kierstead et al. | 536/9 |
| 3,939,144 | 2/1976 | Radobolja et al. | 536/9 |
| 3,950,360 | 4/1976 | Aoki et al. | 260/343.2 R |
| 4,093,629 | 6/1978 | Fisher | 260/343.41 |
| 4,134,973 | 1/1979 | Fisher et al. | 536/17 |

FOREIGN PATENT DOCUMENTS 2717040  11/1977  Fed. Rep. of Germany ............. 536/17

OTHER PUBLICATIONS

"Tetrahedron Letter," vol. 10, pp. 711–714, 1975.
"Jour. of Antibiotics," vol. 29, No. 6, 6/76, pp. 14–16 and pp. 35–42.

*Primary Examiner*—Johnnie R. Brown
*Attorney, Agent, or Firm*—David L. Rose; Harry E. Westlake

[57] ABSTRACT

Derivatives of C-076 are described in which the C-076 molecule, a series of macrolides in which one of the substituents is a 4-(α-L-oleandrosyl)-α-L-oleandrose has one or both of the carbohydrate moieties removed therefrom. The compounds thus produced have profound anthelmintic, insecticidal, ectoparasiticidal and acaracidal activity and compositions for such use are also disclosed.

12 Claims, No Drawings

MONOSACCHARIDE AND AGLYCONE DERIVATIVES OF C-076

CROSS REFERENCE TO RELATED APPLICATIONS

This application is a continuation-in-part of our copending application Ser. No. 838,602, filed Oct. 3, 1977, and now abandoned.

BACKGROUND OF THE INVENTION

The term C-076 is used to describe a series of compounds isolated from the fermentation broth of a C-076 producing strain of *Streptomyces avermitilis*. The morphological characteristics of the culture are completely described in copending U.S. application Ser. No. 772,601 filed Feb. 28, 1977, now abandoned. The C-076 compounds are a series of macrolides, each of which has substituted thereon at the 13-position, a 4-($\alpha$-L-oleandrosyl)-$\alpha$-L-oleandrose group. The C-076 compounds have a very high degree of anthelmintic, insecticidal, ectoparaciticidal and acaracidal activity.

SUMMARY OF THE INVENTION

The C-076 series of compounds have the following structure:

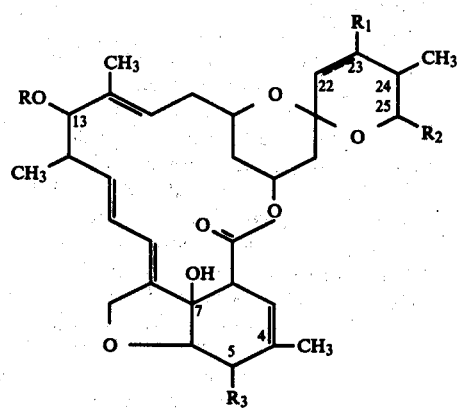

wherein R is the 4'-($\alpha$-L-oleandrosyl)-$\alpha$-L-oleandrose group of the structure:

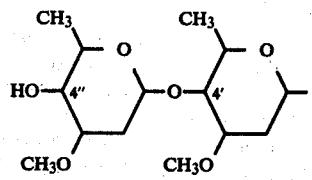

and wherein the broken line indicates a single or a double bond;

$R_1$ is hydroxy and is present only when said broken line indicates a single bond;
$R_2$ is iso-propyl or sec-butyl; and
$R_3$ is methoxy or hydroxy.

There are eight different C-076 compounds and they are given the designations A1a, A1b, A2a, A2b, B1a, B1b, B2a, B2b based upon the structure of the individual compounds.

In the foregoing structural formula, the individual C-076 compounds are as set forth below.

|     | $R_1$       | $R_2$      | $R_3$   |
| --- | ----------- | ---------- | ------- |
| A1a | Double bond | sec-butyl  | —OCH$_3$ |
| A1b | Double bond | iso-propyl | —OCH$_3$ |
| A2a | —OH         | sec-butyl  | —OCH$_3$ |
| A2b | —OH         | iso-propyl | —OCH$_3$ |
| B1a | Double bond | sec-butyl  | —OH     |
| B1b | Double bond | iso-propyl | —OH     |
| B2a | —OH         | sec-butyl  | —OH     |
| B2b | —OH         | iso-propyl | —OH     |

The compounds of the instant invention are realized in the foregoing structural formula when R (the 13-position substituent) is $\alpha$-L-oleandrosyl (the monosaccharide) or hydrogen (the aglycone).

The carbohydrate side chain at the 13-position of the parent C-076 compounds is the 4'-($\alpha$-L-oleandrosyl)-$\alpha$-L-oleandrose group and procedures have been discovered for the selective removal of one or both of the sugar moieties to prepare the C-076 monosaccharide and C-076 aglycone respectively.

The reaction conditions which are generally applicable to the preparation of both the monosaccharide and aglycone involve dissolving the C-076 compound in an aqueous non-nucleophilic organic solvent, miscible with water, preferably dioxane, tetrohydrofuran, dimethoxyethane, dimethyl formamide, bis-2-methoxyethyl ether and the like, in which the water concentration is from 0.1 to 20% by volume. Acid is added to the aqueous organic solvent to the extent of 0.01 to 10% by volume. The reaction mixture is generally stirred at about 20°–40° C., preferably at room temperature, for from 6 to 24 hours. The lower concentrations of acid, from about 0.01 to 0.1% will predominately produce the monosaccharide under the above reaction conditions. Higher acid concentrations, from about 1 to 10% will predominantly produce the aglycone under the above reaction conditions. Intermediate acid concentrations will generally produce mixtures of monosaccharide and aglycone. The products are isolated, and mixtures are separated by techniques such as column, thin layer, preparative layer and high pressure liquid chromatography, and other known techniques.

The acids which may be employed in the above process include mineral acids and organic acids such as sulfuric, hydrohalic, phosphoric, trifluoroacetic, trifluoro methane sulfonic and the like. The hydrohalic acids are preferably hydrochloric or hydrobromic. The preferred acid in the above process is sulfuric acid.

A further procedure for the preparation of the compounds of this invention is applicable to all of the C-076 compounds, however, it is preferred for use on the compounds which contain a 23-hydroxy group, since some degree of addition to the 22,23 double bond is noticed in those compounds with the 22,23 unsaturation. The procedure for the preparation of the monosaccharide uses 1% sulfuric acid by volume in isopropanol at from 20°–40° C., preferably room temperature, for from 6 to 24 hours. For the preparation of the aglycone, 1% sulfuric acid, by volume, in methanol under the foregoing reaction conditions has been found to be appropriate.

The other acids listed above may also be employed for this purpose, at approximately the concentration employed for sulfuric acid.

The above described compounds are isolated from the reaction mixture and mixtures of compounds are separated using techniques known to those skilled in this art, and in particular the chromatographic techniques described above.

The novel monosaccharide and aglycone compounds of this invention have significant parasitical activity as anthelmintics, ectoparasiticides, insecticides and acaricides, in human and animal health and in agriculture.

The disease or group of diseases described generally as helminthiasis is due to infection of an animal host with parasitic worms known as helminths. Helminthiasis is a prevalent and serious economic problem in domesticated animals such as swine, sheep, horses, cattle, goats, dogs, cats and poultry. Among the helminths, the group of worms described as nematodes causes widespread and often times serious infection in various species of animals. The most common genera of nematodes infecting the animals referred to above are Haemonchus, Trichostrongylus, Ostertagia, Nematodirus, Cooperia, Ascaris, Bunostomum, Oesophagostomum, Chabertia, Trichuris, Strongylus, Trichonema, Dictyocaulus, Capillaria, Heterakis, Toxocara, Ascaridia, Oxyuris, Ancylostoma, Uncinaria, Toxascaris and Parascaris. Certain of these, such as Nematodirus, Cooperia, and Oesphagostomum attack primarily the intestinal tract while others, such as Haemonchus and Ostertagia, are more prevalent in the stomach while still others such as Dictyocaulus are found in the lungs. Still other parasites may be located in other tissues and organs of the body such as the heart and blood vessels, subcutaneous and lymphatic tissue and the like. The parasitic infections known as helminthiases lead to anemia, malnutrition, weakness, weight loss, severe damage to the walls of the intestinal tract and other tissues and organs and, if left untreated, may result in death of the infected host. The monosaccharide and aglycone C-076 compounds of this invention have unexpectedly high activity against these parasites, and in addition are also active against Dirofilaria in dogs, Nematospiroides, Syphacia, Aspiculuris in rodents, arthropod ectoparasites of animals and birds such as ticks, mites, lice, fleas, blowfly, in sheep *Lucilia sp.*, biting insects and such migrating diperous larvae as *Hypoderma sp.* in cattle, Gastrophilus in horses, and *Cuterebra sp.* in rodents.

The instant compounds are also useful against parasites which infect humans. The most common genera of parasites of the gastro-intestinal tract of man are Ancylostoma, Necator, Ascaris, Strongyloides, Trichinella, Capillaria, Trichuris, and Enterobius. Other medically important genera of parasites which are found in the blood or other tissues and organs outside the gastrointestinal tract are the filiarial worms such as Wuchereria, Brugia, Onchocerca and Loa, Dracunculus and extra intestinal stages of the intestinal worms Strongyloides and Trichinella. The compounds are also of value against arthropods parasitizing man, biting insects and other dipterous pests causing annoyance to man.

The compounds are also active against household pests such as the cockroach, *Blatella sp.*, clothes moth, *Tineola sp.*, carpet beetle, *Attagenus sp.*, and the housefly *Musca domestica*.

The compounds are also useful against insect pests of stored grains such as *Tribolium sp.*, *Tenebrio sp.* and of agricultural plants such as spider mites, (*Tetranychus sp.*), aphids, (*Acyrthiosiphon sp.*); against migratory orthopterans such as locusts and immature stages of insects living on plant tissue. The compounds are useful as a nematocide for the control of soil nematodes and plant parasites such as *Meloidogyne spp.* which may be of importance in agriculture.

These compounds may be administered orally in a unit dosage form such as a capsule, bolus or tablet, or as a liquid drench where used as an anthelmintic in mammals. The drench is normally a solution, suspension or dispersion of the active ingredient usually in water together with a suspending agent such as bentonite and a wetting agent or like excipient. Generally, the drenches also contain an antifoaming agent. Drench formulations generally contains from about 0.001 to 0.5% by weight of the active compound. Preferred drench formulations may contain from 0.01 to 0.1% by weight. The capsules and boluses comprise the active ingredient admixed with a carrier vehicle such as starch, talc, magnesium stearate, or di-calcium phosphate.

Where it is desired to administer the C-076 derivatives in a dry, solid unit dosage form, capsules, boluses or tablets containing the desired amount of active compound usually are employed. These dosage forms are prepared by intimately and uniformly mixing the active ingredient with suitable finely divided diluents, fillers, disintegrating agents and/or binders such as starch, lactose, talc magnesium stearate, vegetable gums and the like. Such unit dosage formulations may be varied widely with respect to their total weight and content of the antiparasitic agent depending upon factors such as the type of host animal to be treated, the severity and type of infection and the weight of the host.

When the active compound is to be administered via an animal feedstuff, it is intimately dispersed in the feed or used as a top dressing or in the form of pellets which may then be added to the finished feed or optionally fed separately. Alternatively, the antiparasitic compounds of our invention may be administered to animals parenterally, for example, by intraruminal, intramuscular, intratracheal, or subcutaneous injection in which event the active ingredient is dissolved or dispersed in a liquid carrier vehicle. For parenteral administration, the active material is suitably admixed with an acceptable vehicle, preferably of the vegetable oil variety such as peanut oil, cotton seed oil and the like. Other parenteral vehicles such as organic preparation using solketal, glycerol, formal and aqueous parenteral formulations are also used. The active monosaccharide or aglycone C-076 compound or compounds are dissolved or suspended in the parenteral formulation for administration; such formulations generally contain from 0.005 to 5% by weight of the active compound.

Although the antiparasitic agents of this invention find their primary use in the treatment and/or prevention of helminthiasis, they are also useful in the prevention and treatment of diseases caused by other parasites, for example, arthopod parasites such as ticks, lice, fleas, mites and other biting insects in domesticated animals and poultry. They are also effective in treatment of parasitic diseases that occur in other animals including humans. The optimum amount to be employed for best results will, of course, depend upon the particular compound employed, the species of animal to be treated and the type and severity of parasitic infection or infestation. Generally good results are obtained with our novel compounds by the oral administration of from about 0.001 to 10 mg. per kg. of animal body weight, such total dose being given at one time or in divided doses over a relatively short period of time such as 1–5 days. With the preferred compounds of the invention, excellent control of such parasites is obtained in animals by administering from about 0.025 to 0.5 mg. per kg. of body weight in a single dose. Repeat treatments are given as required to combat re-infections and are dependent upon the species of parasite and the husbandry techniques being employed. The techniques for administering these materials to animals are known to those skilled in the veterinary field.

When the compounds described herein are administered as a component of the feed of the animals, or dissolved or suspended in the drinking water, compositions are provided in which the active compound or compounds are intimately dispersed in an inert carrier or diluent. By inert carrier is meant one that will not react with the antiparasitic agent and one that may be administered safely to animals. Preferably, a carrier for feed administration is one that is, or may be, an ingredient of the animal ration.

Suitable compositions include feed premixes or supplements in which the active ingredient is present in relatively large amounts and which are suitable for direct feeding to the animal or for addition to the feed either directly or after an intermediate dilution or blending step. Typical carriers or diluents suitable for such compositions include, for example, distillers' dried grains, corn meal, citrus meal, fermentation residues, ground oyster shells, wheat shorts, molasses solubles, corn cob meal, edible bean mill feed, soya grits, crushed limestone and the like. The active monossacharide and aglycone C-076 compounds are intimately dispersed throughout the carrier by methods such as grinding, stirring, milling or tumbling. Compositions containing from about 0.005 to 2.0% by weight of the active compound are particularly suitable as feed premixes. Feed supplements, which are fed directly to the animal, contain from about 0.0002 to 0.3% by weight of the active compounds.

Such supplements are added to the animal feed in an amount to give the finished feed the concentration of active compound desired for the treatment and control of parasitic diseases. Although the desired concentration of active compound will vary depending upon the factors previously mentioned as well as upon the particular C-076 derivative employed, the compounds of this invention are usually fed at concentrations of between 0.00001 to 0.002% in the feed in order to achieve the desired antiparasitic result.

In using the compounds of this invention, the individual monosaccharide and aglycone C-076 components may be prepared and used in that form. Alternatively, mixtures of two or more of the individual monosaccharide and aglycone C-076 components may be used, as well as mixtures of the parent C-076 compounds and the compounds of this invention.

In the isolation of the C-076 compounds, which serve as starting materials for the instant processes, from the fermentation broth, the various C-076 compounds will be found to have been prepared in unequal amounts. In particular an "a" series compound will be prepared in a higher proportion than the corresponding "b" series compound. The weight ratio of "a" series to the corresponding "b" series is about 85:15 to 99:1. The differences between the "a" series and "b" series is constant throughout the C-076 compounds and consists of a butyl group and a propyl group respectively at the 25 position. This difference, of course, does not interfere with any of the instant reactions. In particular, it may not be necessary to separate the "b" components from the related "a" component. Separation of these closely related compounds is generally not practiced since the "b" compound is present only in a very small percent by weight, and the structural difference negligible effect on the reaction processes and biological activities.

The C-076 compounds of this invention are also useful in combatting agricultural pests that inflict damage upon crops while they are growing or while in storage. The compounds are applied using known techniques as sprays, dusts, emulsions and the like, to the growing or stored crops to effect protection from such agricultural pests.

THe following examples are provided in order that this invention might be more fully understood; they are not to be construed as limitative of the invention.

The C-076 monosaccharide and aglycone derivatives prepared in the following examples are generally isolated as amorphous solids and not as crystalline solids. They are thus characterized analytically using techniques such as mass spectrometry, nuclear magnetic resonance, and the like. Being amorphous, the compounds are not characterized by sharp melting points, however, the chromatographic and analytical methods employed indicate that the compounds are pure.

EXAMPLE 1

A. C-076 Ala Aglycone

1 Mg. of C-076 Ala is dissolved in 0.2 ml. of a mixture of 0.1 ml. concentrated sulfuric acid, 1.9 ml. of methanol and 8.0 ml. of dioxane. The mixture is stirred at room temperature for 16 hours. Thin layer chromatography of the reaction mixture isolates the product which mass spectrometry reveals to be C-076 Ala aglycone.

B. C-076 Ala Aglycone

100 Mg. of C-076 Ala is dissolved in 5 ml. of dioxane, stirred and added at room temperature to a mixture of 0.1 ml. of concentrated sulfuric acid, 1.9 ml. of methanol and 3.0 ml. of dioxane. The reaction mixture is stirred overnight at room temperature. 473 Mg. of solid sodium bicarbonate is added and the mixture stirred for 20 minutes. 3 Ml. of water is added and stirred for an additional 10 minutes. The reaction mixture is concentrated and 40 ml. of chloroform is added and shaken. The aqueous layer is separated and extracted with 5 ml. of chloroform. The organic layers are combined and washed once with dilute sodium chloride solution, dried over magnesium sulfate and evaporated to dryness in vacuo. ½ of the residue is placed on 5 preparative layer chromatography silica gel plates and eluted with 2% methanol in chloroform affording 4 bands of material. The remainder of the material was run on 2 preparative layer chromatography plates eluting with 2% methanol in chloroform affording 4 band similar to the first series. The second fastest bands are removed from each of the plates combined, extracted and evaporated to dryness in vacuo, and rechromatographed on a preparative layer chromatography silica gel plate eluting with 3% tetrahydrofuran and chloroform affording 9.4 mg. of a fluffy white solid which is identified by mass spectrometry as C-076 Ala aglycone.

EXAMPLE 2

C-076 A2a Aglycone

A. A solution of 0.1 ml. concentrated sulfuric acid and 9.9 ml. of methanol is prepared and 0.2 ml. of the solution is combined with 1.0 mg. of C-076 A2a and the reaction mixture stirred at room temperature for 3 days. Thin layer chromatography of the reaction mixture indicates the preparation of C-076 A2a aglycone.

B. 10 Mg. of C-076 A2a is combined with 2.0 ml. of a 1% sulfuric acid in methanol solution and stirred at room temperature for 16 hours. 65 Mg. of solid sodium bicarbonate is added and the mixture stirred for 5 minutes. The solution is evaporated under a stream of nitrogen at 35°-45° C. and 1 ml. of water and 5 ml. of ether is added. The mixture is stirred and the water layer separated and the ether layer dried over magnesium sulfate and evaporated to dryness in vacuo. The residue is placed on preparative layer chromatography silica gel plates and eluted with 19:1 chloroform in methanol. 5 Bands are obtained on the preparative layer chromatography plate and the second fastest is separated and extracted with ether, the ether layer dried and evaporated affording 3 mg. of a solid material which is identified by mass spectrometry as C-076 A2a aglycone.

C. 2 G. of C-076 A2a is combined with 40 ml. of a 1% (volume/volume) solution of concentrated sulfuric acid in methanol. The reaction mixture is stirred at room temperature for 17 hours and diluted with 300 ml. of chloroform. The mixture is washed once with 30 ml. of saturated sodium bicarbonate solution, once with 30 ml. saturated sodium chloride solution, dried over magnesium sulfate and evaporated to dryness in vacuo. 5 Ml. of methanol is added to the residue and allowed to stand at room temperature overnight. Cooling of the mixture in ice causes the slow precipitation of crystals. A supernatant is removed and the solid crystals washed twice with 1 ml. of cold methanol affording 340 mg. of a white solid. The mother liquor and washings are evaporated down to a volume of about 2 ml. and allowed to stand affording an additional crop to crystals. 630 Mg. of a white solid is obtained which is combined with the first batch of crystals and 8 ml. of methanol and evaporated to a volume of 2.5 ml. and allowed to stand for several hours. 910 Mg. of an off white solid is obtained which mass spectrometry identifies as C-076 A2a aglycone.

EXAMPLE 3

C-076 A2a Monosaccharide

500 Mg. of C-076 A2a is dissolved in 10 ml. of a solution of 0.1 ml. of concentrated sulfuric acid and 9.9 ml. of isopropanol. The reaction mixture is stirred at room temperature overnight. 125 Ml. of chloroform is added and the mixture washed once with 10 ml. of saturated sodium bicarbonate and once with 10 ml. of water. The organic layer is dried over magnesium sulfate and evaporated to dryness in vacuo affording a pale yellow solid material which is dissolved in chloroform and placed on 5 preparative layer chromatography silica gel plates and eluted twice with 2% benzene in ethylacetate. The slower moving major fraction contains 367 mg. of a white powder after lyophilization from benzene which mass spectrometry and 300 MHz nuclear magnetic resonance indicates is C-076 A2a monosaccharide.

EXAMPLE 4

C-076 B1a Monosaccharide and C-076 B1a Aglycone 2.5 Ml. of a solution consisting of 0.5 ml. of water 0.5 ml. concentrated sulfuric acid and 9.0 ml. of dioxane is added and the reaction mixture stirred at room temperature for 17 hours. 50 Ml. of ether is added followed by 25 ml. of saturated aqueous sodium bicarbonate solution. The two layer mixture is shaken, the aqueous layer separated and the organic layer washed with water, dried and evaporated to dryness in vacuo. Benzene is added to the residue and the benzene layer is dried and lyophilized affording 60 mg. of yellow material. The material is placed on a preparative layer chromatography silica gel plate and eluted with chloroform-tetrahydrofuran in the volume ratio of 9:1 and 2 bands are observed with an Rf of 0.15 and 0.35. 300 MHz nuclear magnetic resonance identifies the two spots as C-076 B1a monosaccharide and C-076 B1a aglycone respectively. 16 Mg. of each fraction is obtained.

EXAMPLE 5

C-076 B1a Monosaccharide

100 Mg. of C-076 B1a dissolved in 5.0 ml. of tetrahydrofuran and stirred at room temperature while 5.0 ml. of a cold aqueous solution of 10% sulfuric acid (volume/volume) is added dropwise with stirring. The reaction mixture is stirred at room temperature for 18 hours. 75 Ml. of methylene chloride and 25 ml. of saturated aqueous sodium bicarbonate is added and the layers shaken and separated. The organic layer is washed with aqueous sodium chloride solution and an equal volume of water. The organic layer is dried and evaporated to dryness in vacuo affording 70 mg. of a colorless oil. High pressure liquid identifies the residual oil as C-076 B1a monosaccharide.

EXAMPLE 6

C-076 B2a Aglycone

2 G. of C-076 B2a is combined with 40 ml. of a 1% solution of concentrated sulfuric acid in 5 methanol (volume/volume). The reaction mixture is stirred at room temperature for 17 hours. 300 Ml. of chloroform is added followed by 30 ml. of an aqueous saturated sodium bicarbonate solution. The layers are separated and the organic layer washed with 30 ml. of saturated sodium cloride solution, dried over magnesium sulfate and evaporated to dryness in vacuo. 5 Ml. of methanol is added to dissolve the residue and the mixture allowed to stand at room temperature and then cooled in an ice bath, whereupon crystallization occurred. The supernatant is removed and the residue washed twice with 1 ml. portions of cold methanol and the solid crystals dried overnight and then in vacuo at 35° C. affording 1.0 g. of white crystals. A second crop is obtained by evaporating the mother liquors to a volume of 2 ml. and allowing to stand overnight at room temperature. 2 Ml. of methanol is added and the mixture aged in an ice bath affording 140 mg. of a yellow solid. The two solid fractions are combined and dissolved in boiling methanol, about 30 ml. of methanol is required. The solution is filtered hot and concentrated to a volume of about 20 ml. in vacuo whereupon solids begin to precipitate. The solution is filtered hot and the solid materials washed with methanol affording 340 mg. of a white solid. The filtrates are boiled down to a volume of about 8 ml. and set aside to crystallize at room temperature affording 433 mg. of a white solid. Mass spectrometry shows the two fractions to be identical and to be identified as C-076 B2a aglycone.

EXAMPLE 7

C-076 B2a Monosaccharide and C-076 B2a Aglycone

20 Mg. of C-076 B2a is combined with 4 ml. of a solution prepared by combining 0.1 ml. of concentrated sulfuric acid and 9.9 ml. of isopropanol. The reaction mixture is stirred at room temperature for 16 hours, 189 mg. of sodium bicarbonate is added followed by a few drops of water. The volume is reduced to about ½ and 30 ml. of chloroform and 3 ml. of water is added and the mixture shaken. The layers are separated and the aqueous layer extracted with an additional 5 ml. of chloroform. The organic layers are combined, washed once with dilute sodium chloride solution, dried over sodium sulfate and magnesium sulfate and evaporated to dryness in vacuo. The residue is placed on two preparative layer silica gel chromatography plates and eluted twice with 5% tetrahydrofuran in chloroform. 4 Bands of material are observed and individually removed from the preparative chromatography plates. The slowest band affords 7.3 mg. of a white solid which is identified by mass spectrometry as C-076 B2a monosaccharide. The next slowest band affords 1.3 mg. of a white solid and it is identified by mass spectrometry as C-076 B2a aglycone.

What is claimed is:
1. A compound having the formula:

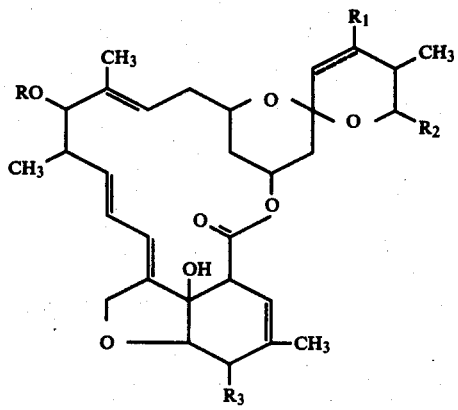

wherein R is hydrogen or α-L-oleandrosyl of the structure:

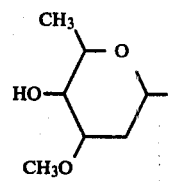

and wherein the broken line indicates a single or a double bond;

$R_1$ is hydroxy and is present only when said broken line indicates a single bond;

$R_2$ is iso-propyl or sec-butyl; and $R_3$ is methoxy or hydroxy.

2. The compound of claim 1 wherein $R_2$ is iso-propyl.
3. The compound of claim 1 wherein $R_2$ is sec-butyl.
4. The compound of claim 3 which is C-076 A1a monosaccharide.
5. The compound of claim 3 which is C-076 A1a aglycone.
6. The compound of claim 3 which is C-076 A2a monosaccharide.
7. The compound of claim 3 which is C-076 A2a aglycone.
8. The compound of claim 3 which is C-076 B1a monosaccharide.
9. The compound of claim 3 which is C-076 B1a aglycone.
10. The compound of claim 3 which is C-076 B2a monosaccharide.
11. The compound of claim 3 which is C-076 B2a aglycone.
12. An anti-parasitic composition which comprises an inert carrier and the monosaccharide or aglycone of C-076.

* * * * *

UNITED STATES PATENT AND TRADEMARK OFFICE
CERTIFICATE OF CORRECTION

PATENT NO. : 4,206,205
DATED : June 3, 1980
INVENTOR(S) : Helmut H. Mrozik et al It is certified that error appears in the above—identified patent and that said Letters Patent is hereby corrected as shown below:

In Example 4 Column 7 line 63 after "added" insert the following:   ---to a mixture of 100 mg of C-076 B1a in 2.5 ml of dioxane---

Signed and Sealed this

Fifteenth Day of February 1983

[SEAL]

Attest:

GERALD J. MOSSINGHOFF

Attesting Officer

Commissioner of Patents and Trademarks